United States Patent
Coulter et al.

(10) Patent No.: US 6,900,029 B1
(45) Date of Patent: *May 31, 2005

(54) METHOD OF SELECTION OF A POPULATION OR SUBPOPULATION OF A SAMPLE UTILIZING PARTICLES AND GRAVITY SEDIMENTATION

(75) Inventors: Wallace H. Coulter, Miami, FL (US); Robert K. Zwerner, Ft. Lauderdale, FL (US); Robert J. Schmittling, Cooper City, FL (US); Thomas R. Russell, Miami, FL (US)

(73) Assignee: Miltenyi Biotec GmbH, Bergisch Gladbach, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/556,667

(22) Filed: Nov. 13, 1995

Related U.S. Application Data

(63) Continuation-in-part of application No. 08/228,791, filed on Apr. 15, 1994, now Pat. No. 5,576,185.

(51) Int. Cl.[7] .......................... A01N 1/02; G01N 33/53; G01N 33/574; C12Q 1/18
(52) U.S. Cl. .......................... 435/30; 210/222; 210/515; 210/520; 210/695; 365/39; 424/1; 435/2; 435/7.2; 435/7.21; 435/7.23; 435/7.24; 435/29; 435/30; 435/173.9; 435/174; 435/176; 435/177; 435/182; 435/183
(58) Field of Search ................................. 210/222, 515, 210/520, 695; 422/44; 435/2, 7.21, 7.23, 7.24, 7.25, 971, 240.1, 7.2, 317.1; 436/525, 526, 523, 824; 365/39; 424/1; 800/2

(56) References Cited

U.S. PATENT DOCUMENTS

| 3,928,143 A | 12/1975 | Coughlin et al. |
| 4,016,293 A | 4/1977 | Coughlin et al. |
| 4,048,018 A | 9/1977 | Coughlin et al. |

(Continued)

FOREIGN PATENT DOCUMENTS

| EP | 0 119 692 A | 9/1984 |
| WO | 90/13013 A | 11/1990 |
| WO | 95/28643 A | 10/1995 |

OTHER PUBLICATIONS

Falkenburg et al. (1986) Selective emoval of Clonogenic Neoplastic B Cells from Human Bone marrow Using Anti–HLA–DQ Antibodies and Complement. Exp. Hematol. 14. 101–107, 1986.*

(Continued)

*Primary Examiner*—Lynette R. F. Smith
*Assistant Examiner*—J. Hines
(74) *Attorney, Agent, or Firm*—Elliot M. Olstein; Raymond E. Stauffer

(57) ABSTRACT

A separation procedure for separating a selected desired or undesired population from a biological sample utilizing relatively heavy, dense particles and gravity sedimentation. The particles have one or more reactants bound thereto which are specific to and will bind with the selected population. The particles preferably are mixed with the sample by repeatedly causing the particles to settle through a substantial portion of the sample to bind to the selected population. The particles with the bound selected population then are allowed to preferentially settle in the sample and the supernatant including an enriched population is separated from the particles with the selected population bound thereto. The enriched populations in the biological sample supernatant can be further enriched by multiple removal steps.

18 Claims, 7 Drawing Sheets

U.S. PATENT DOCUMENTS

| | | | | |
|---|---|---|---|---|
| 4,115,535 A | * | 9/1978 | Giaever | 424/1 |
| 4,487,700 A | | 12/1984 | Kanter | |
| 4,788,136 A | * | 11/1988 | Grenier et al. | 435/7 |
| 4,910,148 A | * | 3/1990 | Sorensen et al. | 435/317.1 |
| 5,125,737 A | | 6/1992 | Rodriguez et al. | |
| 5,229,268 A | * | 7/1993 | Pry et al. | 435/7 |
| 5,238,812 A | * | 8/1993 | Coulter et al. | 435/7.2 |
| 5,256,532 A | | 10/1993 | Melnicoff et al. | |
| 5,576,185 A | * | 11/1996 | Coulter et al. | 435/7.23 |

OTHER PUBLICATIONS

Patel et al. (1993) Use of density pertubation to isolate immunologically distinct populations of cells. J. of Immunological Methods. 163. 241–251, 1993.*

Kessler et al. (1987) Large–Scale Purification and Characterization of CD34–Positive Hematopoietic Progenitor Cells. Blood. 70. Supp. 1, 1987.*

Reynolds et al. (1986) Model System for Removing Neublastoma cells from Bovine Marrow Using Monoclonal Antibodies and Magnetic Immunobeads. Cancer Research. 46. 5882–5886, 1986.*

Patel et al., "Use of density perturbation to isolate immunologically distinct populations of cells," *Journal of Immunological Methods*, vol. 163, pp. 241–251 (1993).*

Reynolds, "Model System for Removing Neurblastoma Cells from Bone Marrow Using Monoclonal Antibodies and Magnetic Immunobeads," *Cancer Research*, vol. 46, pp. 5882–5886 (1986).*

* cited by examiner

METHOD OF SELECTION OF A POPULATION OR SUBPOPULATION OF A SAMPLE UTILIZING PARTICLES AND GRAVITY SEDIMENTATION

RELATED U.S. APPLICATIONS

This application is a continuation-in-part of pending application U.S. Ser. No. 08/228,791, filed Apr. 15, 1994 now U.S. Pat. No. 5,576,185.

BACKGROUND OF THE INVENTION

This invention relates generally to the separation of a desired or undesired population or subpopulation from a sample to obtain the desired population or subpopulation alone or an enhanced population or subpopulation with one or more undesired subpopulations removed therefrom. More particularly, the invention is directed to separating the desired or undesired population or subpopulation such as cells from bone marrow or blood, by binding the population or subpopulation to relatively dense particles and utilizing gravity sedimentation to separate the population or subpopulation from the remaining sample supernatant, including a plurality of separation steps.

The enhancement of a population or a subpopulation of a sample such as hematopoietic stem cells (HSC) can be utilized for many types of applications. The sample can be from bone marrow aspirates, vertebral body marrow (VBM), blood (including peripheral, mobilized or cord blood) or other sources from human or other animals, such as rats, mice, dogs, pigs, cows or primates. The term "mobilized" refers to treatment of a patient with appropriate stimulators to enhance the number of HSC cells. Thus, reducing the amount of sample which must be obtained from a patient by bone marrow aspirations or blood pheresis to obtain a sufficient population of HSC. In addition to enhancement of a population or subpopulation, it is often necessary to remove undesired populations or subpopulations. For example, in bone marrow, the removal of all non-Hodgkin's B lymphoma cells can be desired in the case of a B cell lymphoma. If the bone marrow is to be purged of the B cells and reinfused into the patient, it is important that the bone marrow be completely purged and that the bone marrow be not otherwise damaged.

Currently, one approach is to utilize a plurality of magnetic microspheres, typically formed of a polymer based magnetic material of a relatively low density. The microspheres are desired to be of a relatively low density, because the microspheres are mixed with the bone marrow or blood and specifically are designed not to settle out by gravity sedimentation. The microspheres are typically of a small size, generally about or less than one micron in diameter. However, one product sold by Dynal, Inc. of Great Neck, N.Y., utilizes magnetic polymeric microspheres having a nominal diameter of 2.8 or 4.5 microns with a low microsphere density on the order of 1.5 gm/cc. The prior art magnetic microspheres are intended to be maintained in suspension in the sample and consequently are designed for very slow or substantial elimination of gravity settling in the sample suspension.

The magnetic microspheres have at least one antibody bound thereto specific to the population or subpopulation desired to be removed. Often, such as in the Dynal process, a first monoclonal antibody is bound to the cells of interest and a second antibody specific to the first monoclonal antibody is bound to the microspheres. The cells typically are isolated from whole blood or bone marrow and then washed prior to binding the monoclonal antibody thereto, which washing step causes a non-discriminant loss of cells. The microspheres and cells then are mixed together to bind the microspheres to the cells via the first and second antibodies. For purging blood or bone marrow, a sample would be mixed with a plurality of the antibody bound microspheres and then placed in a magnetic field. The remaining sample or supernatant is removed while the microspheres are held in the magnetic field. This procedure typically must be repeated, since a single purging step generally will not deplete a sufficient percentage of the undesired population or subpopulation(s). The goal of purging is to remove all (100%) of the targeted population or subpopulation. This generally is not feasible and the sample is purged as close to one-hundred (100) percent as is feasible.

The magnetic removal procedure presents several problems. The procedure also removes a number of cells nonspecifically from other populations during each removal step. This decreases the yield, i.e., the percent of the desired population remaining. A single removal step results in a varying yield of a relatively low percent with each succeeding step also reducing the yield. Further, the magnetic microspheres are relatively expensive.

The magnetic microsphere procedure also has been utilized for enhancing a subpopulation for study of the subpopulation. In this case, the magnetic microspheres are bound to the desired subpopulation and the microspheres with the cells bound thereto are removed from the sample. The subpopulation then can be studied directly or can be removed from the microspheres for study. This procedure is time consuming, on the order of about one (1) to six (6) hours or longer, and arguably does not result in a native subpopulation, since the subpopulation has had at least one monoclonal antibody bound to at least one type of cell antigen.

A further use for purging is the study/enhancement of a specific subpopulation, such as the CD4 population of the lymphocytes (L). In this case the microspheres have monoclonal antibodies bound thereto specific to one or more non-CD4 populations. The removal of the other populations enhances the number of CD4 cells in the total remaining cell population in the sample. However, when the magnetic microspheres are utilized, the nonspecific removal of a portion of the CD4 subpopulation can seriously effect the remaining number of the CD4 subpopulation. The non-specific removal of cells can become more of a problem when a large sample volume is being utilized, such as five (5) ml and larger, which volume then requires a large number of the magnetic microspheres. When the magnetic microspheres then are placed in a magnetic field, non-specific trapping and removal of other non-targeted cells often occurs.

Other methods of positive or negative selection, including antibody labeled surfaces, have been used for generating subpopulations of cells from a mixture of different cell types. These methods usually have antibody covalently attached to a plastic surface or to polymer particles in a column. In general, the mixed cell population is combined with the attached antibody, either by adding them to a column and letting them incubate or by letting them settle onto a surface. These procedures work optimally when the red blood cells (RBC's) and plasma have been initially removed from the mixed cell population by preparation of a buffy coat or a mononuclear preparation by density gradients, washing the cells and combining them with the antibody labeled surface. Both methods also require preparation of the separation system and washing with a buffer prior to use, which with incubation times of thirty to sixty (30–60) minutes with the antibody, results in a procedure which takes a minimum of three hours for the column and flask method. These methods can be used for either negative selection or positive selection for the cell population of interest. In both methods, direct separation results in a highly enriched population with resultant loss of non-targeted cells non-specifically. The released cells may have antibody on the cell surface and often are activated by the separation technique, which often is not desirable.

The method and apparatus embodying the invention can be utilized with a variety of immunological reactions, such as immunological reactions involving reactants and cells, virus or biological particles, such as platelets. As utilized herein, cells are defined as animal or plant cells, including cellular bacteria, fungi, which are identifiable separately or in aggregates. Cells are the least structural aggregate of living matter capable of functioning as an independent unit. For example, cells can be human RBC and white blood cell (WBC) populations, cancer or other abnormal cells from tissue, bone marrow and/or from blood samples. Cells suitably tagged or labeled, reasonably can be expected to be operated on by the method and apparatus of the invention in the same manner as the human blood cell or bone marrow examples.

As utilized herein, the term "reactant" defines various molecule(s), such as monoclonal or polyclonal antibodies, which detect and react with one or more specific complementary molecule(s), such as antigens, which are on the surface of a cell. Some examples are given below:

| Reactant | Specific Molecule |
|---|---|
| Antibody | Antigen |
| Drug | Drug Receptor |
| Hormone | Hormone Receptor |
| Growth Factor | Growth Factor Receptor |
| Lectin | Carbohydrate Molecule |
| Nucleic Acid Sequence | Complementary Nucleic Acid Sequence |
| Enzyme | Cofactor or Inhibitor |

The reactants couple or bind to the specific molecule(s) on the cells.

It would be desirable to have an effective method of purging or selecting one or more subpopulations without effecting the remaining populations in a sample, such as whole blood or bone marrow. The method should be inexpensive, fast, result in a high yield even after multiple selection steps or rounds and not be restricted in the volume of sample to be acted upon.

SUMMARY OF THE INVENTION

The invention provides a method and apparatus for separating a desired or undesired population or subpopulation from a biological fluid sample, such as whole blood, quickly and with a high yield. A plurality of dense, relatively heavy particles having one or more reactants, such as monoclonal or polyclonal antibodies, bound thereto are mixed with the sample. The antibodies bound to the particles can be directed at the cells which are not of interest. The particles with the cells bound thereto are allowed to differentially settle by gravity and then the remaining sample is removed. This enhances the number of remaining cells of interest in the sample which were not targeted by the particles. The invention provides a high yield of the cells of interest even after multiple removal steps. The antibodies bound to the particles also can be directed at the cells of interest. The remainder of the sample fluid and non-targeted cells then can be removed from the particles with the targeted cells bound thereto and analyzed to determine how many non-targeted cells were removed. The targeted cells also then can be removed from the particles for further analysis. A preferable particle material of interest can be nickel. The nickel particle can be heated to sterilize the particle where desired. If the sample has been purged and is to be transplanted into a human, a magnetic field and washing procedure can be utilized to remove RBC's and further ensure that all the dense particles have been removed from the sample.

DETAILED DESCRIPTION OF THE PREFERRED EMBODIMENTS

Figure 1:
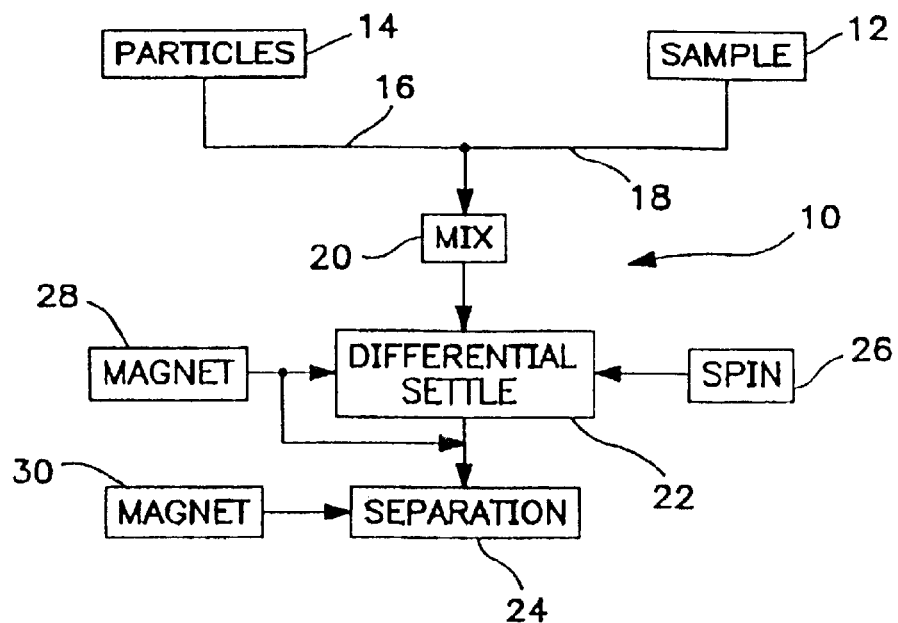
FIG. 1 is a schematic block diagram of a first embodiment of a selection method according to the present invention.

Referring now to FIG. 1, a first embodiment of a selection method and apparatus according to the invention is designated generally by the reference numeral 10. The selection apparatus 10 includes a fluid sample 12 containing a preselected population or subpopulation to be enhanced or removed as desired. The population or subpopulation can be a population or subpopulation of cells, including: cells found in bone marrow, vertebral body marrow (VBM) or blood, such as, neutrophils (N's), eosinophils (E's), monocytes (M's), lymphocytes (L's), lymphocyte subsets, immature cells from stem cells to mature leukocytes, and diseased cells, such as human or animal cancer cells or biological particles such as platelets (PLT's).

The fluid sample can be a biological fluid, including whole blood or a portion thereof, bone marrow, spinal fluid or urine, or other fluids containing populations or subpopulations, such as described above.

The separation apparatus 10 also includes a source of particles 14. The particles 14 include a monoclonal or polyclonal antibody bound thereto, which will bind specifically to selected cells. The antibody can be bound to the particles 14 directly, either covalently or by adsorption, or indirectly via a second antibody in any conventional manner. A plurality of the particles 14 and at least a portion of the sample 12 are combined via respective lines 16 and 18 in a mixing station 20. The combined sample portion and the particles 14 are mixed and then allowed to differentially settle by gravity sedimentation as shown by a block 22. The sample 12 and particles 14 are mixed to facilitate the rapid binding of the particles to the selected cells of interest. The mixing of the sample 12 and the particles 14 is effected to cause the particles 14 to rapidly contact the selected cells in the sample 12. An advantage of the dense particles 14 is that they differentially will gravity settle through the sample 12 following mixing without substantial trapping of non-selected or non-targeted cells. During mixing, another advantage of the particles 14, is that the mixing is performed to cause the particles 14 to repeatedly pass or settle through the sample to provide cell particle binding without physically damaging the cells with the particles 14. For small volumes, on the order of microliters, the mixing can be rapid such as vortexing as disclosed in U.S. Pat. No. 5,238,812, which is incorporated herein by reference. For large volumes, on the order of 0.5 ml to liters, an effective mixing method is to tumble the particles 14 and the sample 12 in an end over end fashion.

Once the particles 14 have been mixed with the sample 12, the particles 14 are allowed to settle to the bottom of a container (not illustrated), then the remaining sample fluid and cells can be separated as illustrated by a block 24. The particles 14 have a density sufficiently greater than the populations in the sample 12, both targeted and non-targeted, that the particles 14 and the targeted populations bound thereto will settle differentially through the sample 12, leaving the unbound/non-targeted populations in suspension. For example, if the sample 12 is a blood sample, the blood cells have a density on the order of 1.05 gm/cc, thus the particles 14 should be substantially more dense than the cells, at least on the order of two (2) to three (3) times more dense than the cells. The remaining sample fluid and cells can be removed for study, where the selected cells of interest have remained in the fluid and have been enhanced and are not bound to the particles 14. The bound particles 14 and cells also can be removed from the remaining sample fluid for removal of the cells from the particles 14, if desired, for study or utilization of the bound cells where they are also cells of interest. The remaining fluid and cells also can be reinfused into a living organism, without the particles and cells bound thereto, which are desired to be eliminated from the sample or fluid.

The apparatus 10 can be an automatic device combining the sample 12 and the particles 14 and moving them between the stations or can be a manual procedure, such as carried out by an operator utilizing a test tube or container for the stations 20, 22 and 24 or can be a combination of the two procedures.

Also, while the settle and separation steps 22 and 24 preferably can be accomplished by gravity separation alone, additional steps can be included, where desired. The sample 12 and the particles 14 can be briefly spun, illustrated by a block 26, to accelerate the settling step 22. The particles 14 also can be of a magnetic material. With the magnetic particles 14, a magnet or a magnetic field, illustrated by a block 28, can be applied to the bottom of the container (not illustrated) to accelerate the settling step 22. Additionally, the magnetic field 28 can be maintained or can be applied to the bottom of the container to ensure that the particles 14 are not removed in the separation step 24. The remaining sample can be removed and can be passed by or through a magnetic field 30 to insure that no particle fragments or particles 14 remain in the fluid sample, such as when the sample is to be reinserted into a living organism, such as the human body.

Figure 2:
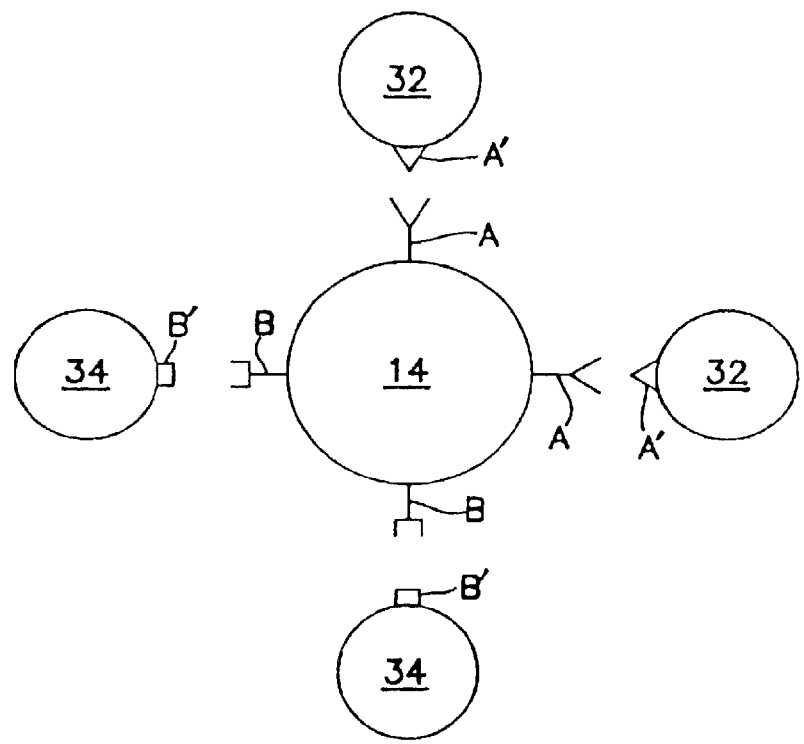
FIG. 2 is a conceptual embodiment of a particle with targeted cells bound thereto in accordance with the present invention.

Referring now to FIG. 2, a conceptual diagram illustrates one particle 14 having two different antibodies A and B bound thereto. For example purposes, a pair of A positive cells 32 are illustrated including at least one antigen A', which specifically will bind with one bound antibody A on the particle 14. A pair of B positive cells 34 also are illustrated including at least one antigen B', which specifically will bind with one bound antibody B on the particle 14. In reality, there would be no particular order to the cell binding and there generally would be an A or a B positive cell blocking the view of the particle 14 on both free sides of the particle 14 (not illustrated). Also, the A & B antibodies on one particle 14 bind to a single cell expressing both the A' and B' antigens. For example, if the A cell was a CD4 positive cell and the B cell was a CD8 positive cell, then there would be four or five A cells and only one or two B cells bound to the particle 14. This ratio exists since the order of binding correlates approximately to the proportion of cells present. In a normal sample, the ratio of CD4 to CD8 positive cells is about 2 to 1. Although, two different antibodies A and B are described as both bound to the particle 14, each antibody can be bound to separate particles 14 as desired.

Again, as before stated, the targeted or selected cells can be removed from the sample 12 bound to the particles 14 and then the cells can be removed from the particles 14 for a separate study of the cells. The cells can be removed from the particles 14 by conventional technology, such as biochemical separation or mechanical disruption methods.

Although no specific particle 14 is critical, a magnetic high density particle 14 is preferable. One preferable particle 14 is formed from carbonyl nickel, such as nickel powders made by INCO as Nickel Powder Type 123. The particles 14 preferably are made with a nominal diameter of about five (5) microns with a preferable range of three (3) to thirty-five (35) microns, but not limited thereto. The fines (smaller fragments) are eliminated prior to utilization. The particles 14 are relatively heavy, having a density preferably on the order of nine (9) gm/cc. The density of the particles is selected such that the particles will differentially settle through the sample suspension more rapidly than the cells. Thus, the targeted cells bound to the particles will be gravity separated prior to any significant isolation by settling of the unbound (non-targeted) cells. Clearly, the greater the differences in density between the sample populations and the particles 14, the faster the differential settling will occur.

The volumes of the sample fluid vary, depending upon the procedure being performed. For analysis of blood, bone marrow or spinal fluids, as little as ten (10) microliters can be utilized, while for clinical transplantations, such as bone marrow, the volumes can range from about one hundred (100) milliliters to three (3) liters. The bone marrow procedures typically are purge procedures to eliminate unwanted cells from the bone marrow fluid. In whole blood or bone marrow, many procedures can be utilized, such as stem cell isolation by elimination of the other blood cells by binding them to one or more monoclonal antibodies bound to one or more of the sets of particles 14.

One preferred method of mixing the particles 14 with the sample 12 is to gently tumble the particles 14 and sample mixture end over end causing the particles 14 repeatedly to fall through the sample 12 to bind to the population of interest. This appears preferable but the familiar roller rocking or stronger mixing procedures can also be effective, if physical damage to the cells of interest by the heavy, dense particles 14 is avoided. One such device can be a test tube holder which rotates slowly to rotate the test tube or similar vessel end over end. This allows a "gentle mixing" of the particles 14 and sample 12 in which the particles 14 mix and settle through a substantial portion of the sample on each rotation allowing the targeted cells to bind to the particles with no apparent physical damage to the cells. The same mixing motion can be obtained by rotating or oscillating the tube back and forth with each end being first on top and then on the bottom, similar to the end over end rotation. The speed of the roller rocker also can be set to effect substantially the same mixing procedure.

One embodiment of a blood bag end over end mixer is illustrated in FIGS. 3A–3E and designated generally by the reference numeral 40. A blood bag (not illustrated) is inserted into the mixer 40 by releasing a top 42 and a bottom 44 holder portion. The top 42 and bottom portion 44 include a snap closure 46 holding the portions together. The top and bottom portions 42, 44 also preferably are hinged together by a hinge 48.

Figure 3A:
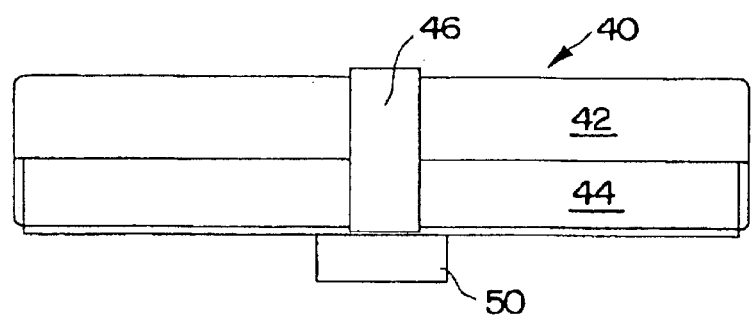
FIGS. 3A–3E are front, side and end views of a blood bag mixer of the present invention.
Figure 3B:
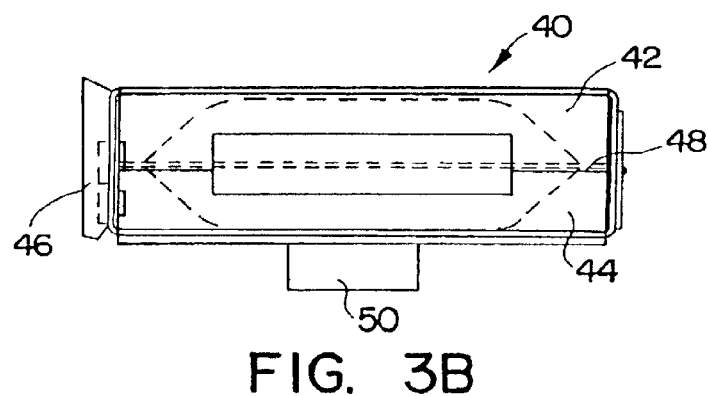
Figure 3C:
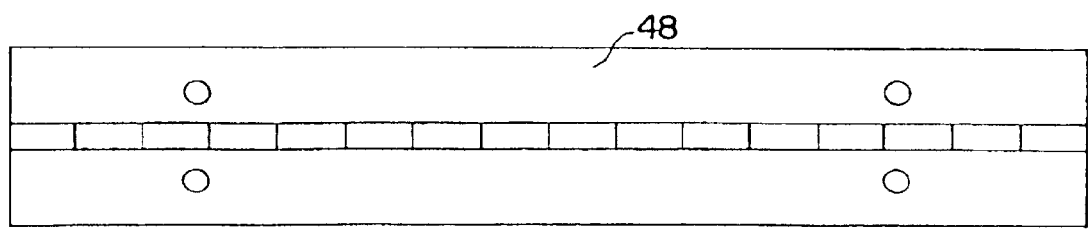
Figure 3D:
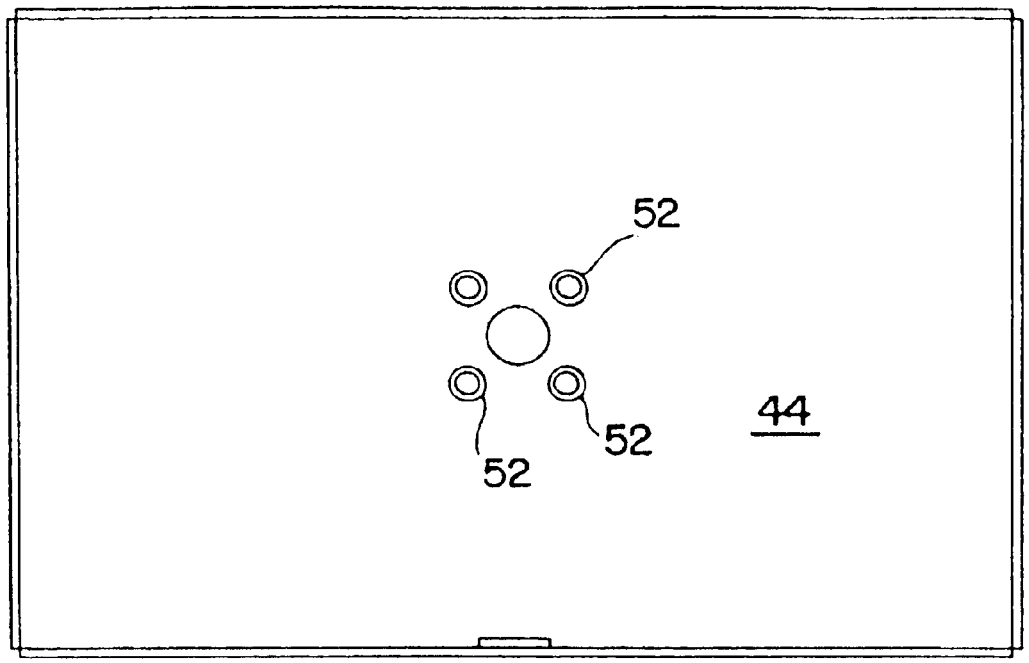
Figure 3E:
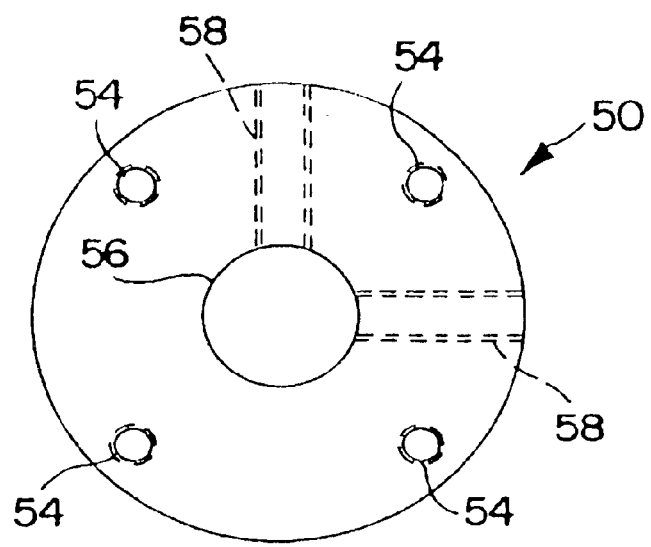

Although illustrated in a horizontal position in FIGS. 3A and 3B, the mixer 40 would be oriented substantially vertically to provide the desirable end over end tumbling of the sample fluid 12 and the particles 14. The mixer 40 can be mounted onto a substantially horizontal motor shaft axis (not illustrated) by a bracket 50 (FIG. 3E). The bracket 50 is attached to one portion 44 of the mixer 40.

The bracket 50 can be attached to the portion 44 through a plurality of apertures 52 (FIG. 3D) formed in the portion 44. The bracket 50 includes a plurality of mating passageways 54 (FIG. 3E), which can be aligned with the apertures 52 and the bracket 50 then can be mounted and secured by a plurality of bolts or other fasteners (not illustrated). The bracket 50 is mounted by a passageway 56 to a motor shaft (not illustrated) for rotation therewith through one or more threaded passageways 58. A bolt (not illustrated) can be threadedly inserted into the passageway 58 to bear against the motor shaft to rotate the mixer 40.

Like the blood tube, the blood bag in the mixer 40 is rotated slowly and the particles are caused to mix and settle through a substantial portion of the sample on each rotation to bind to the targeted cells in the sample.

A first so-called direct method of labeling particles with antibody that is effective in depleting specific subpopulations of cells from a sample mixture, i.e. whole blood, bone marrow, mixed cell populations or body fluids, and due to the density of the particles, readily differentially settling by gravitational force, thereby removing the specifically attached cells along with the particles is set forth hereinafter.

Materials:

Nickel particles—obtained from Novamet Specialty Products Corp. (Wyckoff, N.J. 07481) a lot of INCO (Suffern, N.Y. 10901) Nickel Powder Type 123. This lot had been screened through 400 mesh to remove large particle and air classified as coarse. The resulting lot was Fisher sized at 5.7 microns with a surface area of 0.34 sq meters/gm of particles.

Buffer A—Tris/NaCl, pH 7.2
  9.55 gm/L Tris
  4.0 gm/L NaCl
  combine in $dH_2O$; bring to pH 7.2 with conc. HCl
Buffer B—Tris/NaCl/BSA
  Add to Buffer A, Bovine Serum Albumin (BSA) 0.2 gm/100 ml Antibody Solution—From Table 1 for particle labeling, determine the amount of antibody that will be needed to add to the particles. Calculate the volume of the stock solution of antibody that will result in the requisite amount of purified antibody required. Measure the amount of the stock solution and add it to Buffer A just prior to addition to the particles.

Methods:
1. Weigh out the nickel particles (calculate 1 gm of particles/0.34 $m^2$ surface area).
2. Wash the particles twice with $dH_2O$
    2a. Add $dH_2O$ to the particles and mix by vortexing and inverting the tube.
    2b. Separate the particles from the fluid by allowing them to settle for approximately two minutes and removing the fluid.
3. Wash the particles as in step 2 using a solution of 1% bleach.
4. Wash the particles as in step 2 with Buffer A.
5. Optimally mask the nickel particles with BSA.
    5a. Resuspend the particles to a volume of 2 ml/gm of particles in Buffer A.
    5b. Add an amount of 50 mg/ml BSA solution (1:4 dilution of Buffer B) to result in a final concentration of 3 mg BSA/$m^2$ of particle surface.
    5c. Place the tube on a roller for 3–6 hours at room temperature.
    5d. Wash the particles twice, as in step 2, with Buffer A with 30–60 minutes on the roller between washes.
6. Addition of antibody to the particles.
    6a. Resuspend the 'masked' beads, Step 5, to 1 ml/gm beads.
    6b. Sonicate the beads while adding the antibody solution previously prepared.
    6c. Rinse the tube in which the Antibody Solution was made with Buffer A and combine this with the particles.
    6d. Bring the volume up to 1 ml/gm with Buffer A.
7. Place the tube on a roller and roll the particle/antibody solution overnight at room temperature.
8. Blocking the labeled particles with BSA.
    8a. Wash the particles twice with Buffer A, as in step 5d.
    8b. Add a volume of Buffer B at 2 ml/gm to the particles.
    8c. Resuspend the particles by sonication and vortexing.
    8d. Roll the particles for one hour.
    8e. Replace Buffer B twice with rolling for 30 minutes between exchanges.
9. Storage of the labeled beads.
    9a. Remove the final blocking Buffer B.
    9b. Add fresh Buffer B up to a volume of 2 ml/gm.
    9c. Store the antibody coated beads in a capped tube at room temperature.
10. Testing of antibody/particle preparation.
    10a. Add graded amounts of antibody/particles to test tubes, usually in the range of 10–200 $\mu l$ antibody/ particles per ml of whole blood.

10b. Wash the antibody/particles three times with 3× volume of a mixture of Isoton II (Coulter Diagnostics) and Glucose (4.5 gm/L).

10c. Decant the IG solution and add 1 ml of whole blood (collected in either EDTA or Heparin anticoagulant).

10d. Mix by end-over-end tumbling for 4–5 minutes.

10e. Place the tubes vertically in a test tube holder for 4–5 minutes.

10f. Transfer the blood above the particles with a pipette to another tube (the pipette may be held against a magnet during this transfer to remove nickel particles that may not have settled during step 10e).

10g. Analyze, by the best method for the population being depleted, and compare the residual cells to the original population present in the original sample.

10h. Choose an amount of particles that will be required per ml of whole blood to effectively remove the population of cells in question.

The invention is adapted particularly to bind microspheres/particles/beads to platelets (PLT's) and to WBC populations or WBC subset populations. As utilized herein, WBC subset populations are subsets of a WBC population to which specific monoclonal antibodies can be bound. A nomenclature has been defined for the monoclonal antibodies by the World Health Organization and the International Immunology Society. The monoclonal antibodies are defined by a cluster designation (CD) nomenclature which defines a particular specificity for a cell or group of cells and the monoclonal antibodies specific for that CD group. For example purposes only, the CD groups have been specified in the following table along with the Coulter antibody designator, with the antibody amounts given for the above-referenced first direct label technique.

TABLE I

ANTIBODY AMOUNTS FOR PREPARATION OF NICKEL PARTICLES FOR DEPLETION

| PARTICLE LABELS | ANTIBODY/DESIGNATOR (AMT/M$^2$) |
|---|---|
| Platelet | CD41 PLT-1 (3 mg) |
| B cell | CD20 B1 (9 mg) |
| | CD19 B4 (3 mg) |
| VLA-4 | CD29 4B4 |
| MY | CD14 MY4A (10.5 mg) |
| | CD33 MY 9 (4.5 mg) |
| MT4 | CD2 T11 (6.75 mg) |
| | CD5 T1 (4.6 mg) |
| | CD7 3A1 (2.25 mg) |
| | CD26 TA1 (1.5 mg) |
| T4 | CD4 T4 (5 mg) |
| T8 | CD8 T8 (5 mg) |
| KC-48 | CD15 KC-48 (5 mg) |
| CLASS II | I3 or I2 (5 mg) |

The use of the particles 14 depends both on the density of the particles 14, which allows for rapid settling through a solution and also on the specificity of the selected antibody which allows for attachment of antibody bound particles to specific antigens. A second, improved direct labeling procedure stipulates the conditions for adsorption of antibody onto the nickel particles 14, as follows:

Materials:

1—1 Tris/NaCl Buffer.

1-2 Tris/NaCl/0.2% HSA (Human Serum Albumin) Buffer.

1-3 Monoclonal antibody concentrate.

1-4 Nickel particles, INCO Type 123.

Procedure:

2-1 Determine the amount of the nickel particles 14 that will be utilized by weighing the nickel particles (calculate 1 gm of particles/0.34 m$^2$ of particle surface area).

2—2 Heat the particles at 250° C. for 3 hours with mixing periodically, such as every hour and allow the particles to cool before utilization.

2-3 Dilute the appropriate amount of antibody that will be added to the nickel particles 14 into the Tris/NaCl, pH7.2 buffer (total volume during labeling will be 1 ml/gm of particles).

2-4 Measure the amount of the antibody concentrate and add to the Tris/NaC1 buffer to yield a suspension of 1 gm particles/ml of buffer (add antibody at 5 mg/ml particles).

2-5 Place suspension in an appropriate mixer, such as a roller mixer and mix overnight at room temperature.

2-6 Allow the particles to settle to the bottom of the suspension.

2-7 Decant supernatant and replace with the Tris/NaC1 buffer to yield a suspension of 3 ml/gm of the particles 14.

2-8 Mix the suspension for an appropriate time, such as 30 minutes, to allow antibody to equilibrate.

2-9 Wash the particles 14 by repeating steps 2-6 to 2-8.

2-10 Allow the particles 14 to settle to the bottom of the suspension.

2-11 Resuspend the particles 14 in the Tris/NaC1/0.2% HSA buffer at 2 ml/gram of particles.

2-12 Mix the suspension for 30 minutes.

2-13 Repeat steps 2-10 to 2-12 an additional two times to block nonspecific binding sites.

2-14 Store the antibody labeled particles at 2–8° C. in the Tris/Nc1/0.2% HSA buffer.

The above procedure also can be utilized to produce particles labeled with polyclonal antibody, such as goat anti-mouse immunoglobulin (GAM). These GAM particles then can be utilized in a so-called indirect antibody labeling method, in which the particles 14 are labeled with desired monoclonal antibodies via binding of the monoclonal antibody to the polyclonal antibody on the particle surface. In this case, labeling is done with 5 ug monoclonal antibody/30 ul GAM particles/ml whole blood or cell suspension.

1. Wash appropriate volume of GAM-nickel particles with Tris/NaCl three times to remove any free GAM.

2. Add the Tris/NaCl buffer along with the selected antibody to the particles (100 ul/30 ul of particle suspension).

3. Incubate on appropriate mixer for 20 minutes at room temperature.

4. Wash the particles to remove unbound antibody.

5. Utilize the particles for depletion of the selected cell population.

It is possible to add more than one antibody to a single GAM particle. An example would be CD14 and CD4 bound together on a particle 14 to deplete M's.

Some antibodies do not bind well to particles, such as the nickel particles 14. To prevent free antibody and potential failure of the binding of the particles to the cell population of interest, such antibodies preferably are fixed on the particles, for example, utilizing glutaraldehyde as follows:

Glutaraldehyde Fixation:
1. Wash previously labeled particles twice in $H_2O$.
2. Resuspend with a solution of 0.25% glutaraldehyde in $H_2O$ (use 6 ml/g solids).
3. Incubate on appropriate mixer, such as a roller mixer, for 30 minutes.
4. Wash three (3) times with $H_2O$.
5. Wash once with appropriate buffer.
6. Resuspend to original volume (0.5 g/ml) with buffer/protein(?).
7. Store the particles at 2–8° C.

The above improved method of labeling the particles 14 with antibody, is both effective in depleting specific subpopulations of cells from a sample mixture, so-called negative selection (i.e. whole blood, bone marrow, VBM or mixed cell populations) and, due to the density of the particles, also is effective for removal of specific bound cells along with the particles, so-called positive selection.

EXAMPLE 1

Preparation of Granulocyte Population from Whole Blood

Figure 4A:
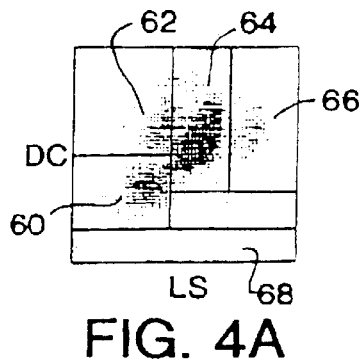
FIGS. 4A and 4B respectively are whole blood control and granulocyte enriched histograms obtained in accordance with the present invention.

A portion of a whole blood sample collected in EDTA was run on a Coulter STKS instrument (which removes RBC's by lysing) as the control for the following depletions, as illustrated in FIG. 4A. The control illustrates the normal WBC population patterns utilizing DC (Coulter volume) and light scatter (LS) parameters, including populations of L's 6Q, M's 62, granulocytes (N's 64 and E's 66) and a debris portion 68. The appropriate amount of nickel particles coated with antibody and previously tittered, were placed in a 12×75 mm glass test tube and washed three times by gravity settling with a solution of Isoton II (Coulter Corporation) containing 4.5 gm/L of glucose (IG buffer). Three milliliters of the whole blood sample was added to the washed particles and the tube capped. The tube was then placed on an end-over-end roller at approximately 30 rev/min. This was found to be appropriate to keep the particles in suspension, allowing the particles to repeatedly fall through the blood. The blood and particles were mixed on this roller for four minutes. Following the mixing, the tubes were removed and set vertically in a test tube rack for four minutes to provide the differential gravity settling. To analyze the remaining populations, the blood above the particles was transferred by a pipette into another tube. In some cases the pipette barrel was held against a magnet to ensure removal of Ni fines which may not have settled out. The samples were then run on a Coulter STKS instrument and compared against the whole blood control. One description of such an operation is disclosed in U.S. Pat. No. 5,125,737, which is incorporated herein by reference. Although the particles and whole blood are mixed and the particles bound to the WBC population or subset population, the RBC's in each case are removed by lysing prior to obtaining the illustrated results. The platelet and RBC results referred to herein are obtained utilizing only a Coulter volume (DC) parameter in instrument channels separate from the WBC channel.

Figure 4B:
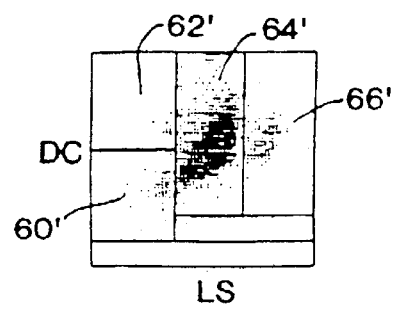

The whole blood sample portion was depleted utilizing the following labeled nickel particles: MY4 200 µl/ml, T4 100 µl/ml, B1 100 µl/ml, PLT-1 80 µl/ml, T8 50 µl/ml and 3A1 50 µl/ml. This mixture of antibody bound labeled particles depleted most of the M's 62', L's 60' and platelets to give an enriched population of granulocytes (N's 64' and E's 66') as illustrated in FIG. 4B. The depletion resulted in a 86% reduction of the platelets, and clearance of the M 62' and L 60' populations in the depleted sample, as compared to whole blood (FIG. 4A). This resulted in a cell preparation consisting of 98% granulocytes 64' and 66' which was 91% of the original granulocyte number. RBC's were retained at 91% of the control whole blood sample, indicating the specificity of the cell depletion.

EXAMPLE 2

Figure 5A:
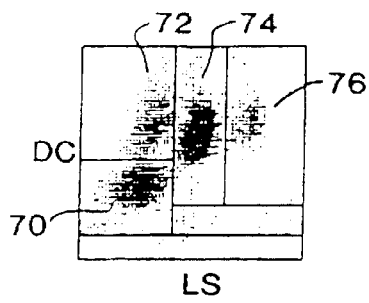
FIGS. 5A and 5B respectively are whole blood control and lymphocyte enriched histograms obtained in accordance with the present invention.
Figure 5B:
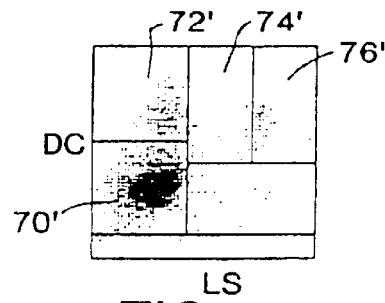

Lymphocyte Preparation using Nickel Particles with Distribution and Retention of Lymphocytes A lymphocyte preparation was made using antibody coated nickel particles as illustrated in FIGS. 5A and 5B. Results of a whole blood control run on a Coulter STKS hematology analyzer are illustrated in FIG. 5A. The normal pattern resulted in 27 percent L's 70, 9 percent M's 72, 61 percent N's 74 and 2 percent E's 76. A combination of the appropriate amount of Ni particles previously labelled with PLT-1 (70 µl particles/ml blood), KC-48 (50 µl particles/ml blood) and MY-4 (100 µl particles/ml blood) for 10 ml of whole blood was placed in a 15 ml polystyrene test tube and washed three times with IG buffer. The supernatant from the last wash was removed and 10 ml of whole blood which had been collected in EDTA was added to the particles. The particles were resuspended in the blood and placed on an end-over-end roller for four minutes. Following the mixing, the tube was placed vertically in a test tube rack and left for four minutes to allow the particles to differentially settle. After the particles had settled the depleted blood was removed with a plastic transfer pipette and placed in a new tube. During the transfer the barrel of the transfer pipette was held against a magnet which removed any nickel fines. Analysis of the lymphocyte preparation on a Coulter STKS hematology analyzer (FIG. 5B) demonstrated a lymphocyte population enhanced to 92 percent. The reduction of the other populations of cells as compared to the whole blood (FIG. 5A) demonstrated a reduction of the platelets of 94%, the N's 74' of 98%, the M's 72' of 80%, the E's 76' of 95% and the RBC's of 1%. This demonstrated the resultant depleted sample was composed of L's 70' with very little non-specific removal (greater than 99% retention of the lymphocytes).

EXAMPLE 3

Recovery of T8 Cells from Antibody Labeled Nickel Particles After Depletion of Whole Blood Nickel particles labeled with T8 antibody were initially used to deplete whole blood of T8 lymphocytes. T8 labeled nickel particles at a suboptimal dose for depletion (15 µl vs. 50 µl/ml of whole blood) were washed three times in IG buffer. Whole blood was added to the particles and placed on an end-over-end roller for ten minutes, and set vertically for five minutes. The depleted blood was removed, and the particles and bound cells were washed twice by resuspending in a volume equal to half the original amount of sample with IG buffer inverting lightly and the particles and bound cells allowed to settle out. Following the washing, the particles/cell pellet was resuspended in IG buffer and placed on a magnetic stirrer for mechanical disruption for about thirty seconds. The disruption results in separating the cells from the particles. The supernatant was separated from the particles by allowing the particles to settle out, removed by pipette and analyzed by flow cytometry. Three samples were analyzed; a whole blood control, the blood following depletion with the T8 labeled particles and the supernatant with released cells after the particles/cells had been stirred and the particles allowed to settle. The results on the Profile II demonstrate the normal appearance of the depleted blood with a slight, 16%, reduction of the lymphocyte population. The recovered cells, however, demonstrate a highly enriched and purified lymphocyte population. Following analysis with the fluorescent surface markers for T4 and T8 the depleted blood had the T8 population reduced from 26% to 6.3%, however, the T4 population was increased from 52.5% to 66.1% due to the decrease in the T8 cells. In the recovered population over 96% of the cells were T8 positive.

EXAMPLE 4

Labeling Various Types of Dense Particles

STUDY A: Different types of dense particles listed in Table II were labeled by the present method with T8 antibody. The standard procedure for labeling Nickel Type 123 particles was used for the various types of particles which included blocking with 3–30 mg/m² BSA and labeling with 5 mg/m² of T8 antibody. Following the labeling and washing T8 depletion of whole blood was carried out in the normal method with titering the amount of labeled particles added. Following a four minute mixing of the blood and particles, the particles were allowed to settle for four minutes. The resulting depleted samples were then analyzed on a flow cytometer (Coulter Profile II) for percent T8 cells. Depletion was calculated as the percent of T8 cells remaining compared with the T8 value of whole blood. Nickel Type 123 is the particle used for the other experiments and was the comparator for the other types of particles. From the titering, 25 μl of the Type 123 particles per ml of whole blood, resulted in over 96% depletion of the T8 cells. A stainless steel particle did not deplete, even at 100 μl of particles/ml of whole blood. Zinc dust, labeled with T8 antibody, resulted in coagulation of the whole blood, probably due to interacting with the EDTA anticoagulant and causing fibrinogen activation by freeing up calcium in the sample. Other types of nickel particles did result in depletion but not as effective as the Type 123.

STUDY B: Several different types of particles, labeled with T4 antibody but not using a BSA precoat step, were tested for labeling by determining their ability to bind to cells. All particles bound antibody, as determined by this method. Pd and VM63-Ni were equivalent or slightly better in binding to cells than Type 123-Ni, but settled slowly: TiO₂, Pb and VM63-Ni were all effective in labeling cells for microscopic identification. Only Ta was demonstrated to be ineffective in binding to cells after being labeled with antibody.

STUDY C: Particles were labeled with KC-48 antibody, specific for neutrophils, by the standard procedures for Type 123-Ni particles. The particles were then mixed with whole blood, a blood smear made and stained and examined using a microscope. All these particles demonstrated specific binding to the neutrophils.

In summary, almost all of the metallic particles tested provided at least some degree of antibody adsorption. However, in the context of depletion ability, Type 123 Nickel was most advantageous due to its surface properties and settling rates. As an example, palladium and manganese dioxide particles would deplete well, but failed to settle rapidly enough solely by gravity settling to be effective in the present invention. Antibody adsorbed to titanium dioxide particles provided efficient tagging of cells for microscopic identification, but due to small size did not result in significant differential settling in whole blood.

TABLE II

| MATERIAL | DESIG-NATION | MANU-FACTURER/ CATALOG/ LOT NO. | PHYSICAL AND MAGNETIC CHARAC-TERISTIC | DEPLE-TION ABILITY |
|---|---|---|---|---|
| Study A: | | | | |
| NICKEL | TYPE 123 | Novamet/ 3451313 | IRREGULAR | +++ |
| NICKEL | VM 63 | Novamet/ VM63 | ULTRAFINE POWDER | +++ |
| NICKEL | 10/585A | Novamet/ 10/585A | SPHERES | ++ |
| NICKEL | HDNP | Novamet/ 347355 | POWDER | ++ |
| STAINLESS STEEL | P316L | Ametek/ 0813290 | IRREGULAR SHAPE | – |
| ZINC DUST | | Aldrich/ HY13401CY | NON-MAGNETIC | * |
| Study B: | | | | |
| NICKEL | TYPE 123 | Novamet/ 3451313 | | +++ |
| NICKEL | VM 63 | Novamet/ VM63 | ULTRAFINE POWDER | +++ |
| NICKEL | 8/209A | Novamet/8/ 209A | SPHERES | ++ |
| NICKEL | 08841R | Spex Ind./ 08841R | POWDER | ++ |
| NICKEL | 01509 BW | Aldrich/ 01509BW | POWDER | ++ |
| NICKEL | 347355 | Novamet/ 347355 | POWDER | ++ |
| Pd | D13A17 | John Matthey Elec./D13A17 | | ++++ |
| TiO₂ | ANATASE | | NON-MAGNETIC | – |
| Ta | SGQ | Noron Metals Div./ SGQ-2-3764 | | + |
| SiO₂ | | | NON-MAGNETIC | + |
| NiO₂ | NO4990 | Pflatz & Bauer/ 040291 | NON-MAGNETIC | ++ |
| Study C: | | | | |
| Pd | D13A17 | John Matthey Elec./D13A17 | Approx. 0.5μ diameter | ++++ |
| TiO₂ | ANATASE | | Approx. 1.0μ diameter | – |
| MnO₂ | | Aldrich/ 23,094-4 | POWDER | ++ |
| Ta | SGQ | Norton Metals Div./ SGQ-2-3764 | POWDER | + |

*Zinc added to whole blood resulted in coagulation

EXAMPLE 5

Depletion of T4 and t8 Subpopulations of Whole Blood Utilizing Antibody Labeled Nickel Particles Nickel particles were labeled with either T4 or T8 antibody using the above referenced procedure for antibody labeling. For depletion, the particles (50 μl/ml whole blood) were transferred to a test tube and washed three times with IG buffer. Following removal of the third wash, whole blood was added to the particles and the combination was mixed, in an end-over-end manner, for four minutes. Following mixing, the tubes were placed in an upright position and the particles were allowed to settle for four minutes. The depleted blood was then labeled with T4-RD1/T8-FITC fluorescent antibody (Coulter Corporation, Coulter Cytostat, part no. 6603802) and assayed on a flow cytometer (Coulter Profile II). All samples were counted for one minute and the populations of the different quadrants were compared for T4 and T8 lymphocytes. As compared to the whole blood control, when T4 particles were used, 94% of the T4 population was depleted while only 18% of the T8 was removed. When T8 particles were used 96% of the T8 population was depleted while only 4% of the T4 population was removed.

EXAMPLE 6

Differential Settling

Figure 6A:
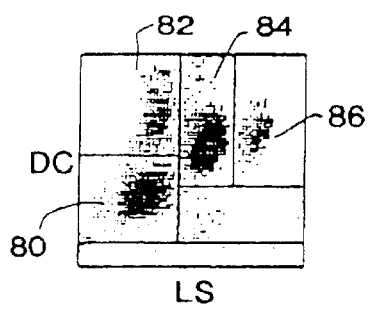
FIGS. 6A–6C are histograms comparing the gravity settling of Rhone-Poulenc magnetic particles with the dense particles of the present invention.
Figure 6B:
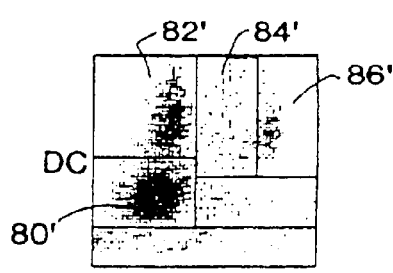
Figure 6C:

FIGS. 6A–C illustrate the differential settling results of the dense particles of the present invention contrasted with the prior art Rhone-Poulenc magnetic particles. FIG. 6A again illustrates a control histogram on a STKS, including a normal population pattern of L's 80, M's 82, N's 84 and E's 86. FIG. 6B illustrates the pattern resulting from a nickel particle depletion utilizing particles with a KC48 monoclonal antibody label. The N's 84 were 59.6 percent of the WBC control population results illustrated in FIG. 6A, while the N's 84' have been reduced to 2.3 percent of the WBC populations illustrated in FIG. 6B.

Rhone-Poulenc particles were utilized in a similar manner as the nickel particles and show virtually no gravity settling as illustrated by the histogram of FIG. 6C. In particular, the bound N's and Rhone-Poulenc particles show a pattern 88, while the unbound Rhone-Poulenc particles appear as a noise or debris pattern 90. Rhone-Poulenc publications assert "that without any magnetic field no significant sedimentation takes place for several hours", indicating again that these particles are designed to prevent gravity settling.

EXAMPLE 7

Mixing Times

The mixing times and methods can be varied according to the sample volume and the desired incubation times. For volumes on the order of 0.5 ml or less, both rapid mixing such as vortexing or nutating and end over end settling of the dense particles can effectively be utilized without physical damage to the cell populations. Vortexing was accomplished utilizing separate antibody bound particles KC48-Nickel (50 $\mu$l/ml WB) and PLT-Nickel (100 $\mu$l/ml WB) with the Coulter STKS results illustrated in Table III. In Table III and each of the other similar tables, such as Tables V, VIII, IX, X and XII, the platelets and WBC's are summarized in units of $10^3/\mu$l, while the RBC's are in units of $10^6/\mu$l.

TABLE III

|   | WBC | N | L | M | PLT | RBC |
|---|---|---|---|---|---|---|
| A) | 5.6 | 2.8 | 2.1 | 0.5 | 230 | 4.09 |
| B) | 4.1 | 1.4 | 2.1 | 0.4 | 91 | 4.19 |
| C) | 3.4 | 0.7 | 2.0 | 0.5 | 58 | 4.15 |

Example A was a control vortexed for thirty (30) seconds without any particles, Example B included the particles vortexed for fifteen (15) seconds and Example C included the particles vortexed for thirty (30) seconds and settled in each case for four (4) minutes.

In conclusion, the neutrophils were fifty (50) percent depleted and the platelets were sixty (60) percent depleted upon fifteen (15) seconds vortexing, whereas an additional fifteen (15) seconds increased depletion of neutrophils to seventy-five (75) percent and platelets to seventy-five (75) percent. It was also noted that the other cell populations were retained without non-specific losses.

The same blood sample was mixed end over end for varying times as illustrated by Table IV.

TABLE IV

| A) | Control, no particles, 10 min. |
| B) | KC48/PLT, 30–45 sec. |
| C) | KC48/PLT, 1 min. |
| D) | KC48/PLT, 1.5 min. |
| E) | KC48/PLT, 2.0 min. |
| F) | KC48/PLT, 4.0 min. |
| G) | KC48/PLT, 10 min. |

The depletion results obtained by the mixing procedure of Table IV are illustrated in Table V. When the STKS instrument reports a result of 0.0 (N's in Table V, F or G), the actual result is below 0.05, generally greater than 99 percent.

TABLE V

| Results: |   | WBC | N | (% Dep) | L | M | PLT | RBC |
|---|---|---|---|---|---|---|---|---|
| Control | A) | 5.6 | 2.8 |  | 2.1 | 0.5 | 240 | 4.20 |
| 30– sec. 45 | B) | 3.7 | 1.0 (64%) |  | 2.0 | 0.5 | 69 (71%) | 4.08 |
| 1 min. | C) | 3.2 | 0.6 (79%) |  | 1.9 | 0.5 | 39 (84%) | 4.02 |
| 1.5 min. | D) | 2.8 | 0.4 (86%) |  | 1.8 | 0.4 | 37 (85%) | 4.00 |
| 2.0 min. | E) | 2.9 | 0.3 (89%) |  | 1.9 | 0.5 | 14 (94%) | 4.10 |
| 4.0 min. | F) | 2.6 | .0 (>99%) |  | 2.0 | 0.5 | 1 (99.6%) | 4.19 |
| 10 min. | G) | 2.7 | 0.0 (>99%) |  | 2.0 | 0.6 | 0 (>99%) | 4.22 |

For these particles and antibodies, the minimal mixing time appears to be about four (4) minutes. For other particles and antibodies, the mixing time may vary within the scope of the present invention. Clearly, minimal mixing beyond the minimum time may be desirable in some cases and is not detrimental to the present invention.

EXAMPLE 8

Small Sample Volumes

Small volumes of 20 $\mu$l whole blood were nutated with 5 $\mu$l of KC48 nickel particles for four (4) minutes. The results showing elimination of 95 percent of the N's were obtained from a conventional whole blood smear assay as shown in Table VI.

TABLE VI

|   | N | L | M | E |
|---|---|---|---|---|
| Control, no particles | 58 | 27 | 12 | 2 |
| Depleted | 3 | 82 | 11 | 3 |

A second small volume of 10 $\mu$l whole blood was nutated with 1 $\mu$l of KC48 and 2 $\mu$l PLT-1 for four (4) minutes. The results were a 82 percent depletion of granulocytes obtained on a Profile II flow cytometer.

EXAMPLE 9

Removal of Granulocytes and/or Platelets from Sample Preparations

Platelets are a component of whole blood and bone marrow that during preparation of cell suspensions are removed by various methods. The attributes of platelets that make them effective in wound repair is disadvantageous in cell preparation work, i.e. platelet clumping and non-specific adhesion to other cells. Since there are approximately 20–50 platelets per leukocyte in whole blood, removal of the platelets prior to any separation work increases recoverability of the leukocytes, results in a leukocyte profile more closely resembling that of whole blood and decreases the preparation time since the most common method of removing platelets is by three separate low speed centrifugations after the cell suspension is isolated. In a preparation that is to be administered to a patient, removal of platelets prior to freezing would decrease non-specific loss of the cells to be infused and eliminate platelet aggregates. In addition, mature granulocytes contain granuals that upon release may result in shock to a patient upon infusion. By removing both mature granulocytes and platelets, the cell preparation for infusion, either immediate or following freezing would be safer and less problematic for the patient.

Figure 7A:
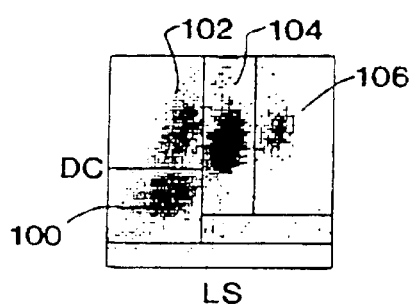
FIGS. 7A and 7B respectively are whole blood control and platelet/granulocyte depleted histograms obtained in accordance with the present invention.
Figure 7B:
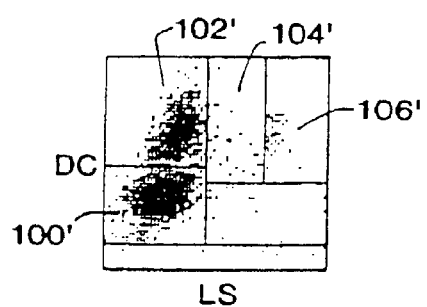

FIG. 7A illustrates a control whole blood population containing L's 100, M's 102, N's 104, E's 106 and platelets (not illustrated). The platelets in the control were $276 \times 10^3$ platelets/$\mu$l, while the granulocytes (N's and E's) were $3.2 \times 10^3/\mu$l. Two sets of dense particles were combined and mixed with the blood for four minutes and settled for four minutes. One set of particles included PLT-1 labeled particles at 80 $\mu$l/ml and the second set of particles included KC48 labeled particles at 50 $\mu$l/ml. As illustrated in FIG. 7B, the L's 100' and M's 102' were effected very little, while the N's 104' and E's 106' were reduced by about 99.9 percent. The platelets were reduced to about $2 \times 10^3/\mu$l.

Figure 8A:
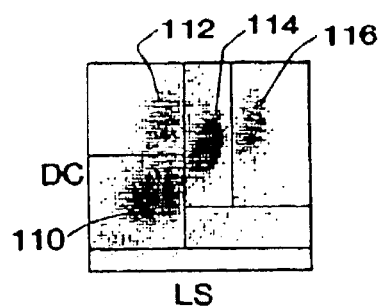
FIGS. 8A–8C respectively are whole blood control and platelet and granulocyte depleted histograms obtained in accordance with the present invention.
Figure 8B:
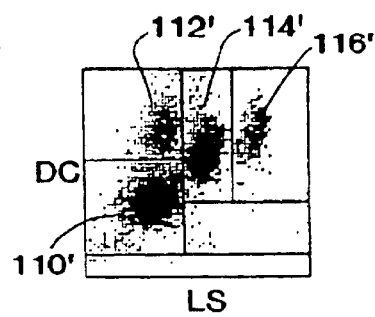

The platelets and granulocytes also can be separately removed in separate blood sample portions. FIG. 8A illustrates a control whole blood population containing L's 110, M's 112, N's 114, E's 116 and platelets (not illustrated). FIG. 8B illustrates a sample portion following depletion of the platelets, again utilizing the PLT-1 labeled dense particles. The platelets were reduced from $231 \times 10^3$ platelets/$\mu$l in the control whole blood population to $3 \times 10^3$ platelets/$\mu$l in the depleted sample portion. The remaining populations L's 110', M's 112', N's 114' and E's 116' were relatively uneffected.

Figure 8C:
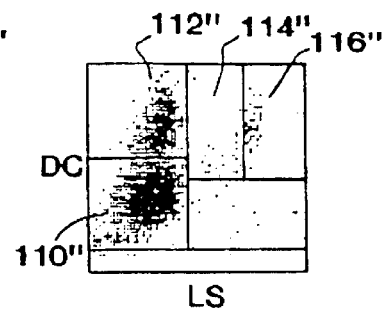

FIG. 8C illustrates a sample portion following depletion of the N's 114 and the E's 116, utilizing KC48 labeled dense particles. The N's 114" and E's 116" were reduced to essentially zero from a total N's 114 and E's 116 of $2.8 \times 10^3/\mu$l. The platelets were relatively uneffected.

EXAMPLE 10

Enhanced Gravity Settling

FIGS. 9A–9F illustrate histograms of gravity settling compared to a brief accelerated settling utilizing the particles of the present invention. FIGS. 9A–9D illustrate a N preparation utilizing the particles with labels listed in Table VII.

TABLE VII

| | |
|---|---|
| T4 | 50 $\mu$l/ml |
| T8 | 50 $\mu$l/ml |
| MY4 | 50 $\mu$l/ml |
| B1 | 50 $\mu$l/ml |
| PLT | 70 $\mu$l/ml |
| I3 | 50 $\mu$l/ml |

FIG. 9A again illustrates a control whole blood population of L's 120, M's 122, N's 124, E's 126, platelets (not illustrated) and RBC's (not illustrated).

TABLE VIII

| FIG. | | SAMPLE | WBC | N | L | M | E | PLT | RBC |
|---|---|---|---|---|---|---|---|---|---|
| 9A | | Control | 6.9 | 4.1 | 2.2 | 0.4 | 0.2 | 288 | 4.87 |
| 9B | dep. | Settle | 4.3 | 3.9 | 0.2 | 0.0 | 0.1 | 35 | 4.59 |
| 9C | spin | Control | 6.9 | 4.1 | 2.2 | 0.4 | 0.1 | 297 | 4.74 |
| 9D | dep. | Spin | 4.3 | 3.9 | 0.2 | 0.0 | 0.1 | 15 | 4.60 |
| 9E | spin | Control | 7.4 | 4.5 | 2.2 | 0.4 | 0.2 | 293 | 4.96 |
| 9F | dep. | Spin | 2.7 | 0.0 | 2.1 | 0.4 | 0.1 | 280 | 4.94 |

Figure 9A:
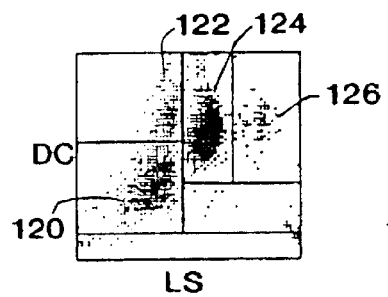
FIGS. 9A–9F are histograms illustrating the results of gravity settling of the present invention compared with accelerated settling of the present invention.
Figure 9B:
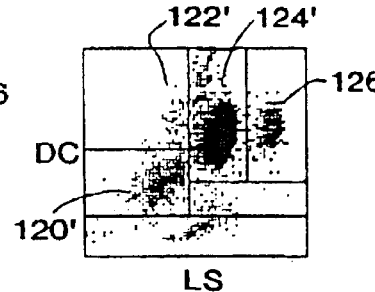

The N preparation utilizing the labeled particles of Table VII results in an enriched N population 124', where the N percentage of the WBC's has increased from 59.7 percent to 89.6 percent. The L's decreased from 32.1 percent to 4.9 percent and the M's decreased from 5.5 percent to 0.8 percent, as illustrated in FIG. 9B.

Figure 9C:
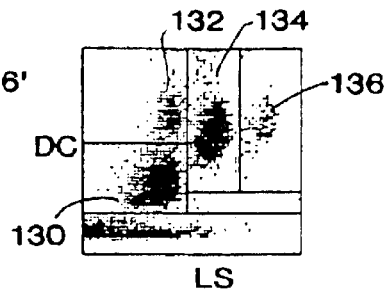
Figure 9D:
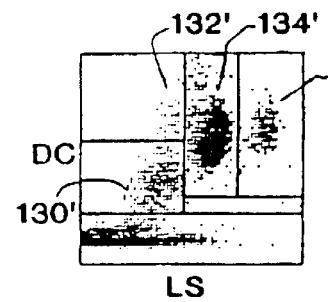

FIG. 9C illustrates a control whole blood population of L's 130, M's 132, N's 134 and E's 136. In this example, instead of gravity settling the sample portion and the particles were centrifuged on a small centrifuge, such as a Fisher Scientific Micro-Centrifuge Model 59A, for 15 seconds at setting No. 2. The brief centrifugation or increased/enhanced gravity settling obtained similar results as the gravity settling in a shorter time period, if desired. The N percent increased from 59.5 percent to 89.1 percent. The L's decreased from 31.5 percent to 5.7 percent, while the M's decreased from 5.8 percent to 0.5 percent as illustrated in FIG. 9D.

Figure 9E:
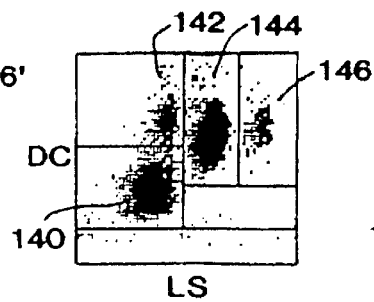
Figure 9F:
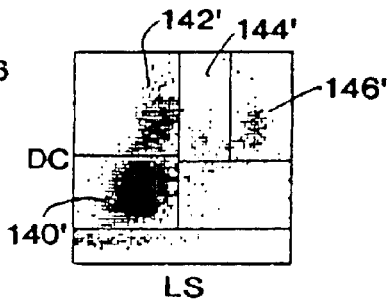

Any single population or subpopulation can be removed utilizing the same procedure, for example, as illustrated in FIGS. 9E and 9F. FIG. 9E illustrates a control whole blood population of L's 140, M'2 142, N's 144 and E's 146. In this example, the N's 144 are removed utilizing the enhanced gravity spinning of the sample and particles. The N's are reduced from 61.4 percent in the control to 0.7 percent as illustrated by 144' in FIG. 9F, while the remaining populations are relatively uneffected.

The primary aspects of the present invention are directed to gravity settling of the dense particles. The enhanced gravity settling, however, could be utilized with the cells in a density gradient system, such as ficoll, in which case the particles would only be required to be slightly more dense than the cells and the gradient system. With the enhanced gravity settling (spinning) the slightly more dense particles and cells bound thereto could be separated in the ficoll gradient system.

EXAMPLE 11

Settling Time

FIGS. 10A–10F illustrate histograms comprising various gravity settling time results of the present invention, which results are summarized in Table IX.

TABLE IX

| FIG. | SAMPLE | WBC | N | L | M | RBC | PLT |
|---|---|---|---|---|---|---|---|
| 10A | Control 4 min | 8.2 | 3.5 | 3.3 | 1.0 | 5.45 | 315 |
| 10B | Depleted 4 min | 5.0 | 0.1 | 3.4 | 1.1 | 5.44 | 315 |
| 10C | Control 2 hr | 8.4 | 3.7 | 3.2 | 1.0 | 5.08 | 350 |
| 10D | Depleted 2 hr | 4.6 | 0.1 | 3.3 | 1.0 | 5.33 | 319 |

TABLE IX-continued

| FIG. | SAMPLE | WBC | N | L | M | RBC | PLT |
|---|---|---|---|---|---|---|---|
| 10E | Control 3 hr | 8.3 | 3.6 | 3.2 | 1.0 | 5.48 | 321 |
| 10F | Depleted 3 hr | 4.6 | 0.0 | 3.4 | 1.0 | 5.31 | 321 |

Figure 10A:
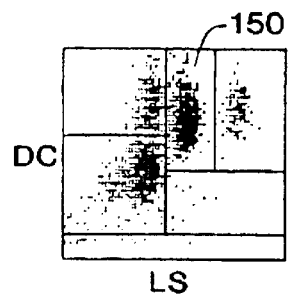
FIGS. 10A–10F are histograms illustrating the results of varying gravity settling times of the present invention.
Figure 10B:
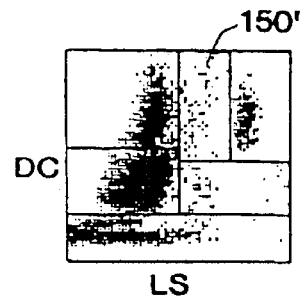
Figure 10C:
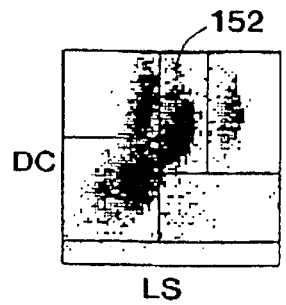
Figure 10D:
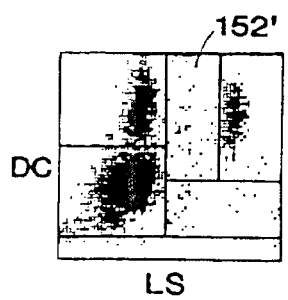
Figure 10E:
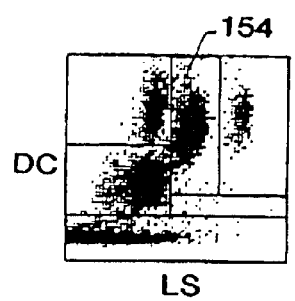
Figure 10F:
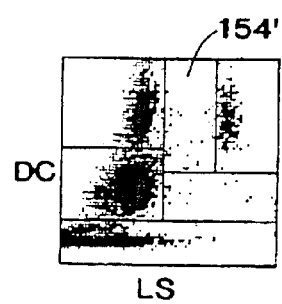

The results of Table IX were obtained by adding 3 ml portions of the same whole blood population sample into four separate tubes or vessels. The first tube was a control tube and each of the other three tubes had 120 μl of KC48 labeled particles added to them. All four tubes were then mixed end over end for four (4) minutes and then allowed to gravity settle for respective times of four (4) minutes, two (2) hours and three (3) hours. The sample portion above the particle was then removed, mixed and analyzed. A control portion (FIGS. 10A, 10C and 10E) was then compared with the respective depleted samples (FIGS. 10B, 10D and 10F). As shown by the FIGURES and Table IX, the control portion whole blood populations were virtually unchanged over the range of four (4) minutes to three (3) hours. Also, as illustrated, the depleted portions for each settling time are substantially the same.

For the four (4) minutes settling example, the N's 150 (FIG. 10A) were reduced from 42.9 percent to the N's 150' (FIG. 10B) of 2.5 percent. Likewise in the two (2) hour settling example, the N's 152 (FIG. 10C) were reduced from 43.5 percent to the N's 152' (FIG. 10D) of 1.1 percent. In the three (3) hour settling example, the N's 154 (FIG. 10E) were reduced from 42.7 percent to the N's 154' (FIG. 10F) of 0.8 percent.

EXAMPLE 12

Particle Heating

Figure 11A:
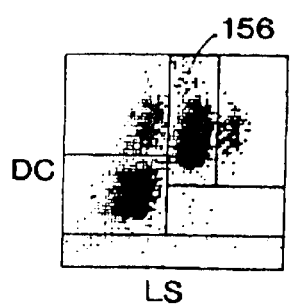
FIGS. 11A–11C are histograms comparing heated particles to non-heated particles of the present invention.
Figure 11B:
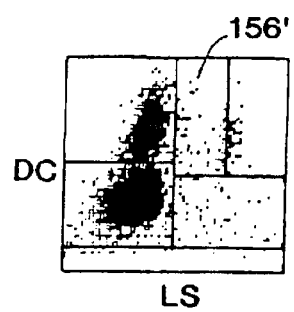
Figure 11C:
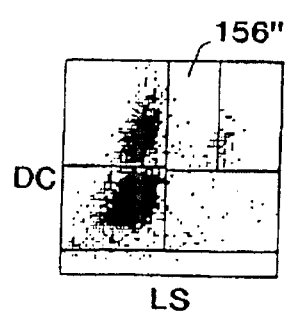

FIGS. 11A–11C illustrate the comparison of unheated Type 123-Ni particles to heated Type 123-Ni particles, as also tabulated in Table X.

TABLE X

| FIG. | SAMPLE | WBC | N | L | M | RBC | PLT |
|---|---|---|---|---|---|---|---|
| 11A | Control | 6.4 | 3.9 | 1.8 | 0.5 | 4.28 | 337 |
| 11B | Unheated | 2.4 | 0.0 | 1.9 | 0.4 | 4.14 | 311 |
| 11C | Heated | 2.4 | 0.0 | 1.9 | 0.4 | 4.19 | 307 |

Again, the results were obtained by utilizing KC48 labeled particles. The other populations were relatively uneffected, while the results of the unheated particles (FIG. 11B) and the heated particles (FIG. 11C) were essentially the same. Prior to adsorption of antibody, the particles were heated to 250° C. for three (3) hours to sterilize (to remove microbes) and to remove endotoxins from the particles, for use especially where a treated sample is to be reintroduced into a patient. Heating the particles also decreases the solubilization of Ni ions from the particles by forming an oxide layer on the surface of the particles. The particles were allowed to settle for four (4) minutes after mixing for four (4) minutes as before. The N's 156 (FIG. 1A) were reduced from 61.8 percent to the N's 156' (FIG. 11B) of 1.4 percent utilizing the unheated particles and to N's 156" (FIG. 11C) of 1.7 percent utilizing the heated particles. In general, the Type 123-Ni particles can be heated in a range of 250° C. to 280° C. for a range of three (3) to five (5) hours. Since the results of the heated and unheated particles were essentially equivalent, the other examples were not repeated and reflect use of unheated particles.

EXAMPLE 13

Improved Cell Preparation for Transplantation

The particles of the present invention also can be utilized to deplete platelets in a bone marrow preparation (prep). Conventional bone marrow processing methods were compared with the particle removal techniques of the present invention as illustrated in Table XI.

TABLE XI

|  | Conventional | Particle/PLT-Depletion |
|---|---|---|
| Percent Recovered After Thawing | 29% | 46% |
| Viability | 95% | 99% |
| Percent Recovery of CFU | 56% | 71% |

The conventional method of bone marrow preparation employs separation over ficoll followed by resuspension and washing of the harvested progenitors with three low speed centrifugations to remove the platelets. The conventional technique example resulted in a 29 percent recovery after thawing of the bone marrow, of which 95 percent were viable and 56 percent of colony forming units (CFU) (or progenitor cells) were recovered. In contrast, the particle depletion of the present invention, which is much faster and less complicated, resulted in a 46 percent recovery after thawing, with 99 percent viability and 71 percent recovery of CFU's. The platelets were separated from the bone marrow with the particles prior to ficoll separation. This eliminated the conventional slow centrifugation washes, reduced platelet/cell aggregates which provided the enhanced CFU recovery. In the example illustrated in Table XI, 30 ml of bone marrow was depleted utilizing 600 μl of PLT-1 labeled nickel particles, mixed end over end and settled, each for four (4) minutes. The sample then was layered over ficoll followed by thirty (30) minutes centrifugation at 600 G. The interface then was harvested and concentrated by centrifugation in Tris/NaCl+0.05% BSA. The recovered cells were resuspended in the culture media RPMI 1640+10% FCS (fetal calf serum). The processed sample then was frozen and thawed to compare to the conventional methodology.

As a further CFU enrichment, a small portion (1.3 ml) of the first platelet depleted bone marrow sample was further depleted utilizing particles labeled with 15 μl of KC48 particles, 50 μl of T11 particles, 50 μl of particles labeled with B1 and B4 and 50 μl of particles labeled with MY4 and MY9. This removed substantially all the lineage positive (mature) cells from the bone marrow. By depleting the mature cells, a highly enriched population of progenitor/stem cells (CFU's) was recovered for analysis. The CFU-GM (granulocyte, monocyte)/$10^5$ cells obtained in a sample before freezing utilizing the conventional prep was 143 CFU-GM and utilizing the particle platelet depletion of the present invention was 147 CFU-GM, while utilizing the further particle lineage depletion of the present invention was 620 CFU-GM.

EXAMPLE 14

Lyophilized Particles

As illustrated by Table XII, lyophilized particles of the present invention also were effective in depleting N's and PLT's. Two sets of particles, one labeled with KC48 and one labeled with PLT-1 were combined to deplete the N's and PLT's.

TABLE XII

| SAMPLE | WBC | N | L | M | PLT | RBC |
|---|---|---|---|---|---|---|
| Whole Blood Control | 7.2 | 4.2 | 2.4 | 0.5 | 207 | 4.33 |
| Whole Blood with lyophilized particles | 3.1 | 0.1 | 2.5 | 0.4 | 6 | 4.45 |

In conclusion, the lyophilized particles appear to be as effective as the non-lyophilized particles. Lyophilized particles could be utilized in kits or other uses, since the lyophilized particles eliminate the requirement of maintaining the particles in solution.

EXAMPLE 15

Class II Population Removal

As illustrated by Tables XIII, the particles 14 also can be effectively utilized to remove the MHC class II positive cells for example, HLA-DR positive cells such as B cells from whole blood, utilizing I3 and/or I2 antibodies.

TABLE XIII

| SAMPLE/I3 OR I2 AND I3 PARTICLES | B1 (CD20) PERCENTAGE |
|---|---|
| Whole Blood | 12.9 |
| I3/10 ul/ml Whole Blood | 5.8 |
| I3/25 ul/ml Whole Blood | 2.2 |
| I3/50 ul/ml Whole Blood | 1.0 |
| I3/100 ul/ml Whole Blood | 0.8 |
| Whole Blood | 11.5 |
| I2 and I3/30 Whole Blood | 1.5 |

The I2 and I3 antibodies were both bound to a single nickel particle 14, as illustrated in FIG. 2.

Figure 12:
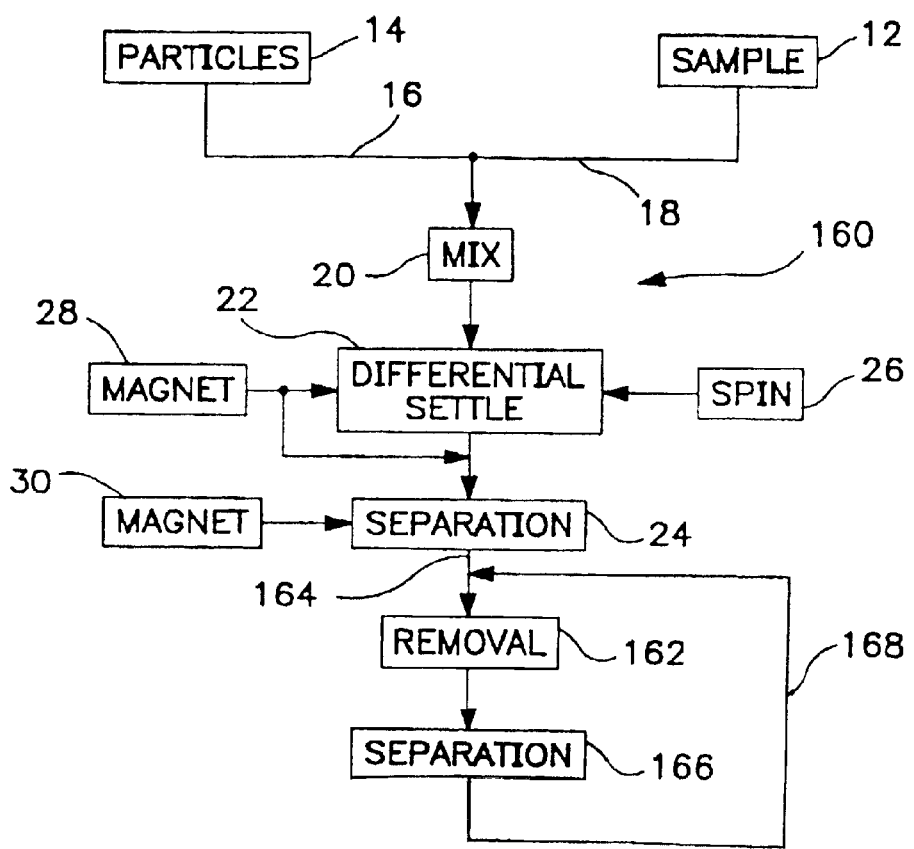
FIG. 12 is a schematic block diagram of a second embodiment of a selection method according to the present invention.

Referring now to FIG. 12, a second embodiment of a selection method and apparatus according to the present invention is designated generally by the reference numeral 160. The selection apparatus 160 includes the identical steps and elements 12–30, as described with regard to the selection apparatus 10 in FIG. 1.

In addition, the selection apparatus 160, includes an additional removal step 162. The removal step 162 can include removal of the residual cells of the cell population or subpopulation previously removed from the sample portion in step 24 and/or can include removal of one or more different populations or subpopulations desired to be removed from the sample portion.

The supernatant or a portion thereof, including the enhanced or enriched population or subpopulation from the separation step 24 is fed via a line 164 to the removal step 162, which removal step can be substantially identical to the steps described with respect to the selection apparatus 10, in FIG. 1. When the additional removal step 162 is completed, the resultant sample supernatant including the further enriched population or subpopulation again can be separated from the particles 14 in a separation step 166. Again the enriched population or subpopulation, can be utilized as is, studied, or further enriched, such as by repeating the steps 162 and 166 as illustrated by a line 168. Again, the residual or different populations or subpopulations can be removed as desired from the resultant sample supernatant.

EXAMPLE 16

Interfering Population

As illustrated by Table XIV, an interfering population(s) or subpopulation(s) can be removed in the separation step 24, followed by a positive or negative selection of a remaining population or subpopulation in the steps 162 and 166. For example, if the population of interest is the Beta chain of the very late antigen (VLA), which is an adhesion molecule, then L's, M's and PLT's are interfering populations. The L's, M's and PLT's interfere since each has VLA and therefore all are positive to a CD29(4B4) antibody. Therefore, when utilizing 4B4 particles, PLT's interfere with both positive and negative selection of the desired (non-PLT) population. The effect of removal and non-removal of PLT's from a whole blood sample is shown in Table XIV.

TABLE XIV

| Sample | M's Percentage | Total 4B4 Percentage |
|---|---|---|
| Whole Blood Control | 7.1 | 25.0 |
| 4B4 | 2.7 | 2.2 |
| PLT and 4B4 | 0.2 | 1.6 |

As can be seen from Table XV, the multiplicity of PLT's (being far greater in number than the other 4B4 positive populations) prevents the M's from being depleted (or selected) resulting in a percentage after 4B4 particle removal of 2.7. Therefore, the PLT's are first removed with a first set of CD41 particles 14 at a concentration of 50 ul/ml of whole blood. The 4B4 positive cells then sequentially are removed with a second set of the particles 14, again at a concentration of 50 ul/ml of whole blood. Since the interfering PLT's substantially have been reduced, the 4B4 particles now can reduce the M's to 0.2 percent. The removal of the PLT's, also allows a lesser number (concentration) of the 4B4 particles to be utilized.

EXAMPLE 17

Multiple Selection Rounds

The high percentage recovery of a specific subpopulation enriched by the techniques of the present invention, for example purposes T4, is illustrated in TABLE XV.

TABLE XV

| Sample/Number of Depletions | WBC | L's | T4 Percentage | T8 Percentage | T4 Count | T8 Count | PLT | RBC |
|---|---|---|---|---|---|---|---|---|
| Whole Blood Control | 4.9 | 1.4 | 47.8 | 31.5 | 669.2 | 441.0 | 213 | 5.0 |
| 1X depleted | 1.7 | 1.0 | 69.4 | 5.1 | 694.0 | 51.0 | 17 | 4.8 |
| 2X depleted | 1.7 | 0.9 | 70.5 | 0.3 | 634.5 | 2.7 | 12 | 4.6 |
| 3X depleted | 1.5 | 0.8 | 72.4 | 0.0 | 579.2 | 0.0 | 9 | 4.5 |

TABLE XV-continued

| Sample/Number of Depletions | WBC | L's | T4 Percentage | T8 Percentage | T4 Count | T8 Count | PLT | RBC |
|---|---|---|---|---|---|---|---|---|
| 4X depleted | 1.2 | 0.9 | 71.5 | 0.0 | 643.5 | 0.0 | 9 | 4.3 |
| 5X depleted | 1.0 | 0.9 | 71.8 | 0.0 | 646.2 | 0.0 | 7 | 4.2 |
| 6X depleted | 1.0 | 0.9 | 71.3 | 0.0 | 641.7 | 0.0 | 5 | 3.8 |

The number of depletions or selection rounds is not limited in number or in populations or subpopulation to be removed. With regard to the number of depletions in the table, the following population and/or subpopulations were removed in the respective depletions from an original sample of ten (10) ml of whole blood. Depletion No. 1 was CD15(KC-48), CD41(PLT-1), CD20(B1), CD8(T8) and CD14(MY4A). Depletion Nos. 2 and 3 were CD8 and CD14. Depletion Nos. 4 & 5 were CD15, while Depletion No. 6 was CD15, CD8 and CD14. As has been stated previously, the populations or subpopulations can be removed sequentially or all at one time. In this example, each antibody was bound to separate sets of the particles 14 and then all the sets were utilized together in one removal operation for each Depletion. As clearly can be seen from Table XV, the T4 subpopulation was enhanced from a percentage of 47.8 to about 71 percent, with an absolute count decreasing only slightly from 669 to 641 or about ninety-six (96) percent recovery after six (6) depletion rounds. The T8's were completely removed after three (3) depletion rounds, while the PLT's were decreased by over ninety (90) percent in one depletion round.

EXAMPLE 18

B-Cell Prep

A B-cell preparation or enhancement from whole blood is shown in Table XVI.

TABLE XVI

| Sample | TI1 | B1 | CD3/T4 | CD3/T8 | G's | M's |
|---|---|---|---|---|---|---|
| Whole Blood Control | 3508 | 516 | 2017 | 985 | 15810 | 2032 |
| Three (3) Depletions | 276 | 545 | 176 | 80 | 41 | 81 |

In this preparation, a buffy coat first was prepared from a heparin whole blood sample and washed once with PBS. The first depletion was CD15(KC48) and CD41(PLT-1). The second depletion utilized indirect antibody labels on a single GAM particle for CD7 (3A1) and CD5 (T1). The third depletion again utilized a single GAM particle for CD14 (MY4A) and CD33(MY9). This preparation enhanced the B cells from 516 to 545 (a statistical variance), while decreasing each of the other depleted populations by greater than ninety-one (91) percent. The G's or granulocytes include the N's and E's.

Many modifications and variations of the present invention are possible in light of the above teachings. It is therefore to be understood that within the scope of the appended claims, the invention may be practiced otherwise than as specifically described.

What is claimed is:

1. A method of enhancing a selected population or subpopulation of cells of interest in a fluid sample having a plurality of populations of cells, comprising:
   providing a plurality of particles having a density at least two times the density of the cells of interest and sufficient to provide differential gravity settling, said particles having bound thereto a reactant which specifically binds to the cells or biological particles of at least one preselected population or subpopulation not of interest;
   mixing a portion of said sample with said particles to bind said particles to said cells or biological particles of said preselected population or subpopulation without substantially physically damaging said cells of said selected population or subpopulation of interest;
   differential gravity settling said particles with said bound population or subpopulation of cells or biological particles in said sample portion, wherein settling is accomplished by gravity separation alone;
   removing at least a portion of the resultant supernatant of said sample portion including said selected population or subpopulation of said cells of interest from said particles and said bound population or subpopulation of cells or biological particles;
   providing a second plurality of particles having a density at least two times the density of the cells of interest and sufficient to provide differential gravity settling, said particles having bound thereto a reactant which specifically binds to the cells or biological particles of at least one preselected population or subpopulation not of interest;
   mixing at least a portion of said removed supernatant of said sample portion including said selected population or subpopulation of cells of interest with said second plurality of particles to bind said second plurality of particles to said second preselected population or subpopulation of cells or biological particles without substantially physically damaging said selected population or subpopulation of cells of interest;
   differential gravity settling said second set of particles with said bound population or subpopulation of cells or biological particles in said supernatant sample portion wherein settling is accomplished by gravity separation alone; and
   removing at least a portion of the resultant second supernatant including said selected population or subpopulation of cells of interest from said second set of particles and said bound population or subpopulation of cells or biological particles and recovering at least fifty percent of said selected population or subpopulation of cells originally in said supernatant sample portion.

2. The method of claim 1 wherein said particles are 2 to 3 times more dense than said cells of interest.

3. A method of enhancing a selected population or subpopulation of cells of interest in a fluid sample, comprising:
   (a) providing a plurality of particles having a density at least two times the density of the cells of interest and sufficient to provide differential gravity settling, said particles having bound thereto at least one reactant which specifically binds to at least one preselected population or subpopulation of cells or biological particles not of interest;

(b) mixing said sample with said particles to bind said particles to said preselected population or subpopulation without substantially physically damaging said population or subpopulation to be enhanced;

(c) permitting said particles and said particles bound to said preselected population or subpopulation of cells to settle via differential gravity settling, leaving a supernatant, wherein settling is accomplished by gravity separation alone; and (d) separating at least a portion of the supernatant comprising said population or subpopulation to be enhanced from said settled particles and said settled particles bound to said preselected population or subpopulation not of interest.

4. The method of claim 3, wherein said reactant is an antibody.

5. The method of claim 4, wherein said antibody is a monoclonal antibody capable of specifically binding to an antigen selected from the group consisting of CD41, CD20, CD19, CD29, CD14, CD33, CD2, CD5, CD7, CD26, CD4, CD8, CD15, I3 and I2.

6. The method of claim 3, wherein said particles have bound thereto two different reactants which specifically bind to two different preselected populations or subpopulations of cells or biological particles not of interest, wherein said reactants are monoclonal antibodies.

7. The method of claim 6, wherein said two different monoclonal antibodies are capable of specifically binding to two antigens selected from the group consisting of CD41, CD20, CD19, CD29, CD14, CD33, CD2, CD5, CD7, CD26, CD4, CD8, CD15, I3 and I2.

8. The method of claim 6, wherein said particles are indirectly bound to reactants via a polyclonal antibody.

9. The method of claim 3, wherein said sample is selected from the group consisting of vertebral body marrow, bone marrow, pheresis blood, and mixed cell populations.

10. The method of claim 3, wherein said selected population of cells of interest comprise hematopoietic stem cells.

11. The method of claim 3, wherein said particles are 2 to 3 times more dense than said cells of interest.

12. The method of claim 11, wherein said particles comprise nickel.

13. The method of claim 3, wherein said volume ranges from 100 milliliters to 3 liters.

14. The method of claim 3, wherein at least 82% of said population or subpopulation of cells to be enhanced originally in said sample, is recovered in said supernatant.

15. The method of claim 3, wherein at least 96% of said population or subpopulation of cells to be enhanced originally in said sample, is recovered in said supernatant.

16. The method of claim 3, wherein more than one preselected population or subpopulation of cells not of interest are removed sequentially or all at one time.

17. The method of claim 3, wherein said steps (a)–(d) are repeated for multiple rounds of enhancement.

18. The method of claim 4, wherein said monoclonal antibody is capable of specifically binding MHC Class II cells.

* * * * *